United States Patent
Osborne et al.

(10) Patent No.: US 10,543,165 B2
(45) Date of Patent: Jan. 28, 2020

(54) METHOD OF IMPROVING THE APPEARANCE OF AGING SKIN

(71) Applicant: The Procter & Gamble Company, Cincinnati, OH (US)

(72) Inventors: Rosemarie Osborne, Oxford, OH (US); Lisa Ann Mullins, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 424 days.

(21) Appl. No.: 14/302,669

(22) Filed: Jun. 12, 2014

(65) Prior Publication Data

US 2015/0023893 A1 Jan. 22, 2015

Related U.S. Application Data

(60) Provisional application No. 61/847,024, filed on Jul. 16, 2013.

(51) Int. Cl.
| | |
|---|---|
| A61K 8/97 | (2017.01) |
| A61K 8/67 | (2006.01) |
| A61K 45/06 | (2006.01) |
| A61Q 17/04 | (2006.01) |
| A61Q 19/08 | (2006.01) |

(52) U.S. Cl.
CPC ............... *A61K 8/97* (2013.01); *A61K 8/675* (2013.01); *A61K 45/06* (2013.01); *A61Q 17/04* (2013.01); *A61Q 19/08* (2013.01)

(58) Field of Classification Search
None
See application file for complete search history.

(56) References Cited

U.S. PATENT DOCUMENTS

| | | | |
|---|---|---|---|
| 3,755,560 A | 8/1973 | Dickert | |
| 4,421,769 A | 12/1983 | Dixon | |
| 5,939,082 A | 8/1999 | Oblong | |
| 5,976,548 A | 11/1999 | Hsia | |
| 2004/0175347 A1 | 9/2004 | Bissett | |
| 2006/0018860 A1 | 1/2006 | Chen et al. | |
| 2006/0275237 A1 | 4/2006 | Bissett | |
| 2007/0196344 A1 | 1/2007 | Osborne | |
| 2008/0305059 A1* | 12/2008 | Chaudhuri | 424/62 |
| 2010/0239510 A1 | 1/2010 | Ha | |
| 2010/0330007 A1* | 12/2010 | Spindler et al. | 424/59 |
| 2011/0262025 A1 | 2/2011 | Jarrold | |
| 2011/0250298 A1 | 10/2011 | Muller | |
| 2012/0283112 A1 | 2/2012 | Binder | |
| 2013/0280187 A1 | 4/2013 | Osborne | |
| 2013/0336906 A1 | 6/2013 | Osborne | |
| 2013/0337087 A1 | 6/2013 | Finlay | |

FOREIGN PATENT DOCUMENTS

| | | |
|---|---|---|
| JP | 2002-212053 A | 7/2002 |
| JP | 2006 206532 A | 8/2006 |
| JP | 2012-82177 A | 4/2012 |

OTHER PUBLICATIONS

International Search Report PCT/US2014/046844; dated Oct. 10, 2014.
Tanaka Y T et al: "Cynaropicrin from *Cynara scolymus* L. suppresses photoaging of skin by inhibiting the transcription activity of nuclear factor-kappa B", Bioorganic and Medicinal Chemistry Letters vol. 23, No. 2,Jan. 15, 2013 (Jan. 15, 2013), pp. 518-523.
Kwon Woon Yong et al: "Niacin attenuates lung inflammation and improves survival during sepsis by downregulating the nuclear factor-[kappa)B pathway.", Critical Care Medicine Feb. 2011, vol. 39, No. 2, Feb. 2011 (Feb. 2011), pp. 328-334.

* cited by examiner

*Primary Examiner* — David J Blanchard
*Assistant Examiner* — Sarah J Chickos
(74) *Attorney, Agent, or Firm* — John G. Powell

(57) ABSTRACT

A method of improving the appearance of aging skin that includes applying an effective amount of artichoke leaf extract and vitamin $B_3$ compound in combination to a target area of skin that exhibits a sign of aging skin, and compositions that include an effective amount of artichoke leaf extract and vitamin $B_3$ compound in combination. The composition is applied for a period of time sufficient for the combination of vitamin $B_3$ compound and niacinamide to improve the appearance of the aging skin.

8 Claims, No Drawings

METHOD OF IMPROVING THE APPEARANCE OF AGING SKIN

FIELD

The present invention relates to methods of improving the appearance of aging skin, especially fine lines and wrinkles, using a synergistic combination of artichoke leaf extract and a vitamin $B_3$ compound.

BACKGROUND

The epidermis, the outermost layer of the skin, comprises a cellular continuum of four layers: the stratum corneum, the granular layer, the spinous layer, and the basal layer. Each cellular layer in the epidermis represents various stages along a process in which basal epidermal keratinocytes undergo a continuous cycle of proliferation, differentiation, and apoptosis, moving upward from the basal layer to finally yield corneocytes. These corneocytes form the cornified layer known as the stratum corneum.

Basal keratinocytes reside at the lower portion of the epidermis. These mitotically active cells undergo a proliferative cycle to generate daughter cells that are physically dislocated upward into the spinous and granular layers and undergo the process of differentiation into corneocytes. On passing through the spinous and granular layers, the cells undergo morphological changes that render them flatter in structure as they lose their cellular viability, undergo alternate keratin expression profiles, and transform into cellular remnants. On average, a younger-aged epidermis turns over in about one month, shedding the older cells and replacing them with newer ones, but this process can increase to over forty days in older skin.

The stratum corneum's corneocytes remain connected to one other via proteins and lipids, creating a protective barrier between the organism and its outside environment. This tightly regulated epidermal permeability barrier functions as a physical and selective barrier against chemical and biological insults Important functions of this barrier include attenuation of the penetration of free radicals and prevention of penetration of harmful radiation, including UV radiation, into deeper layers. The stratum corneum also acts as a permeability barrier and functions to prevent loss of body moisture to the outside environment. Dysfunction of this barrier can lead to chronic skin conditions, diseases, and in extreme cases can even threaten the viability of the organism.

Skin aging is a multifactorial process driven by intrinsic (chronological aging) and extrinsic (environmental) factors, including ultraviolet radiation (UV) exposure (i.e., "photoaging"), environmental toxins, pollutants, and smoking. It is well known in the art that the ability of the stratum corneum to cyclically generate new layers of skin diminishes with age so that the stratum corneum turnover rate is substantially reduced in aged skin, with the cornified layer becoming gradually thinner. This results in a reduction in the functioning capacity of the barrier so that harmful stimuli penetrate the stratum corneum more easily, leading to UV-damage, for example, of the underlying dermal layers, degradation of collagen and elastin, and eventually manifests in appearance as wrinkling and skin atrophy. Thinning of the stratum corneum by the sum of intrinsic and extrinsic aging factors increases the visible appearance of fine lines and wrinkles. Further, the barrier suffers from an age-related increase in permeability to free radicals and a reduction in the amount of lipid in the intercellular matrix, decreasing barrier capacity to diffuse toxins from deeper layers. Recovery capacity of the barrier to environmental insult is also substantially reduced with age.

Thus, the skin's epidermal barrier function is key to the skin's ability to regenerate and protect itself from the appearance of aging signs such as fine lines and wrinkles. Accordingly, it would be desirable to provide compositions and methods of treatment that can improve the skin's epidermal functioning and thus also improve the appearance of aging skin.

SUMMARY

In order to provide a solution to the problems above, disclosed herein are methods of improving the appearance of aging skin. In some embodiments, the method comprises applying a composition with an effective amount of artichoke leaf extract and an effective amount of a vitamin $B_3$ compound to an area of aging skin for a period of time sufficient to improve the appearance of the aging skin. In some embodiments, the area of aging skin may be aging facial skin. In particular embodiments, improving the appearance of aging skin comprises improving the appearance of aging skin texture such as wrinkles, fine lines, coarse deep lines, crevices, bumps; preventing loss of skin elasticity, for example, due to loss, damage and/or inactivation of functional skin elastin, resulting in such conditions as elastosis, sagging, loss of skin recoil from deformation; and combinations thereof.

In response to the problems identified in the background, the present invention may take other forms. Further forms herein will be appreciated in the detailed description that follows.

DETAILED DESCRIPTION

All percentages and ratios used herein are by weight of the total composition and all measurements made are at 25° C., unless otherwise designated. All numeric ranges are inclusive of narrower ranges; delineated upper and lower range limits are interchangeable to create further ranges not explicitly delineated.

The compositions herein can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods. As used in the description and the appended claims, the singular forms "a," "an," and "the" are intended to include the plural forms as well, unless the context clearly indicates otherwise.

"Additive effect" means that the effect provided by a combination of actives is equal to or substantially equal to the sum of their individual effects. For example, an additive effect would be demonstrated when a first active, which provides a 10% improvement in a desired property (e.g., inhibition of NF-κB, which is described in more detail below), when used alone, and a second active, which provides a 20% improvement in the desired property when used alone, provide a 30% improvement to the desired property when used in combination. A "more than additive effect," in this example, would be demonstrated when the combination of the first and second actives improves the desired property by more than 30%.

"Apply" or "application," when referring to a composition, means to apply or spread the composition onto a human skin surface such as the epidermis.

"Cosmetic composition" means a composition suitable for topical application on mammalian skin and/or other keratinous tissue such as hair and nails. Topical means the surface of the skin or other keratinous tissue. Cosmetic composition includes any color cosmetic, nail, or skin care product. "Skin care" means regulating and/or improving skin condition. Nonlimiting examples of skin care include improving skin appearance and/or feel by providing a smoother, more even appearance and/or feel; reducing the oily and/or shiny appearance of skin. Non-limiting examples of cosmetic compositions include products that leave color on the face, such as foundation, mascara, concealers, eye liners, brow colors, eye shadows, blushers, lip sticks, lip balms, face powders, solid emulsion compact, and the like. "Skin care products" include, but are not limited to, skin creams, moisturizers, lotions, and body washes.

"Derivative," as used herein, includes but is not limited to, amide, ether, ester, amino, carboxyl, acetyl, and/or alcohol derivatives of a given compound.

"Dermatologically acceptable" means that a composition or components described are suitable for use in contact with human skin tissue without undue toxicity, incompatibility, instability, allergic response, and the like.

"Effective amount" means an amount of a compound or composition sufficient to significantly induce a positive benefit. For example, an effective amount can mean an amount of artichoke leaf extract and/or vitamin $B_3$ compound sufficient to significantly induce an appearance and/or feel benefit. Effective amount can also mean an amount of artichoke leaf extract and/or vitamin $B_3$ compound in combination sufficient to synergistically increase the inhibition of NF-κB.

"Extract" refers herein to one or more compounds separated from a plant or plant material by contacting the plant with an exogenous solvent (i.e., any solvent that is not inherently present in the plant material) in an extraction process. For example, the extract may be obtained by the following procedure: (i) place the indicated portion of dried plant material (e.g., stem, bark, leaves, etc.) in a conical glass percolator; (ii) add the indicated percentage of extraction solvent in a w/w ratio of 1 part plant material to 2 parts extraction solvent (when the indicated percentage of extraction solvent is less than 100%, the remaining solvent is water (e.g., 95% ethanol with 5% water, 50% ethanol with 50% water, etc.)); (iii) allow the extraction to proceed for about 16 to about 24 hours; (iv) collect the percolate, and repeat the above process until the resulting percolate is substantially free from plant additional extract; (v) combine the percolates, evaporate to dryness under reduced pressure, and store the resulting extract under nitrogen at less than 4 degrees Celsius. Extracts may be used without any further modification or may be modified (e.g., ethoxylated, esterified) to form a derivative material.

"Facial skin surface" means one or more of forehead, periorbital, cheek, perioral, chin, and nose skin surfaces.

"Skin care actives," or "actives," means compounds that, when applied to the skin, provide a benefit or improvement to the skin.

"Synergy" and variations thereof means that the combination of vitamin $B_3$ compound and artichoke leaf extract provides an advantage over using either of the actives alone. In some embodiments, synergy may be demonstrated by the combination of vitamin $B_3$ compound and artichoke leaf extract acting together to provide an anti-aging benefit that is beyond what the combination would normally be expected to provide. For example, if the combination is expected to provide an additive effect, but instead provides a more than additive effect, the combination is synergistic.

"Improving the appearance of aging skin" or "improving the texture of aging skin" means effecting a visually and/or tactilely perceptible positive change, or benefit, in skin texture appearance and/or feel. These terms also include preventing or delaying the appearance of one or more textural signs of skin aging. Benefits that may be provided include, but are not limited to, one or more of the following: improving the appearance of wrinkles, fine lines, coarse deep lines, crevices, bumps; preventing loss of skin elasticity, for example, due to loss, damage and/or inactivation of functional skin elastin, resulting in such conditions as elastosis, sagging, loss of skin recoil from deformation; and combinations thereof.

"Textural signs of skin aging" include but are not limited to, all outward visibly and tactilely perceptible skin texture manifestations, as well as any macro- or microeffects, due to undesired changes in skin texture due to aging. These signs may result from processes which include, but are not limited to, the development of textural discontinuities such as wrinkles and coarse deep wrinkles, fine lines, skin lines, crevices, bumps, unevenness or roughness; loss of skin elasticity; keratoses; abnormal differentiation; hyperkeratinization; elastosis; collagen breakdown, and other histological changes in the stratum corneum, dermis, or epidermis; and combinations thereof.

I. Compositions

The present invention relates to various compositions and, more specifically, to compositions for application to a skin surface including a wide variety of cosmetic compositions. The compositions may be in various product forms that include, but are not limited to, solutions, suspensions, lotions, creams, gels, toners, sticks, pencil, sprays, aerosols, ointments, cleansing liquid washes and solid bars, shampoos and hair conditioners, pastes, foams, powders, mousses, shaving creams, wipes, strips, patches, electrically-powered patches, wound dressing and adhesive bandages, hydrogels, film-forming products, facial and skin masks (with and without insoluble sheet), make-up such as foundations, eye liners, and eye shadows, and the like. The composition form may follow from the particular dermatologically acceptable carrier chosen, if present in the composition.

A. Artichoke Leaf Extract and Vitamin $B_3$ Compounds

Surprisingly, it has been discovered that vitamin $B_3$ compound and artichoke leaf extract, when used in combination, can provide a synergistic improvement in the inhibition of (nuclear factor kappa-light-chain-enhancer of activated B cells) ("NF-κB"). NF-κB is a protein complex found in almost all animal cell types and is known to be involved in a variety of biological process such as, for example, DNA transcription, cellular responses to stimuli such as stress, cytokines, free radicals, ultraviolet irradiation, oxidized LDL, and bacterial or viral antigens. NF-κB's recognized involvement in biochemical pathways associated with skin health and aging make it a suitable indicator of the predictive anti-aging activity of skin care actives. In particular, NF-κB's is known to be involved in the inflammation pathway, which is associated with the skin's barrier function as well as its ability to regenerate and protect itself from the textural signs of skin aging. Accordingly, suitable compositions herein include an effective amount of artichoke leaf extract and vitamin $B_3$ compound in combination. As used herein, "in combination" means present in the same composition (e.g., as a blend), present in different compositions but applied contemporaneously (e.g., close enough in time to result in the combined synergistic benefit of the two materials), or combinations thereof.

The amount of artichoke leaf extract that is "effective" can differ from one particular source (e.g., manufacturer) of extract to another, and can be determined by the skilled artisan based upon the particular extract product's level of activity (e.g., level of active components present). As with any extract, the concentration of active components in the particular extract product to be used will depend on factors such as the final dilution volume of the extract product, the particular extraction method employed, the natural range of variation among individual plants, and other common factors known to those skilled in the art.

Artichoke leaf extract (INCI Name: *Cynara scolymus* extract; CAS number: 84012-14-6) suitable for use herein may be derived from the long, deeply serrated basal leaves of the artichoke plant. These leaves contain higher concentrations of biologically active compounds, such as caffeic acid derivatives (e.g., cynarin); flavonoids; and sesquiterpene lactones (e.g., cynaropicrin). It can be preferable to dry the leaves before extraction in order to achieve greater potency of certain active materials. For example, cynarin is found only in trace amounts in the fresh leaves, but is formed by natural chemical changes that take place during drying and extraction of the plant material. The artichoke leaf extract may include other suitable materials such as, for example, water, thickeners, humectants, solvents, solubilizers, etc. The artichoke leaf extract can be prepared by suitable processes known in the art. An example of a commercially available artichoke leaf extract suitable for use herein is Biobenefity™, made by Ichimaru Pharcos Corp. (Gifu, Japan). In some embodiments, the composition may include artichoke leaf extract in an amount of from 0.0001% to 15%, from 0.0002% to 10%, from 0.001% to 15%, from 0.025% to 10 from 0.05% to 10%, from 0.05% to 5%, or even from 0.1% to 5%, by weight of the total composition.

The present compositions include a vitamin $B_3$ compound. As used herein, "vitamin $B_3$ compound" means a compound having the formula:

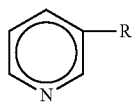

wherein R is —$CONH_2$ (i.e., niacinamide), —COOH (i.e., nicotinic acid) or —$CH_2OH$ (i.e., nicotinyl alcohol); derivatives thereof; and salts of any of the foregoing. The vitamin $B_3$ compound may be present at an amount of from 0.0001% to 15%, from 0.0002% to 10%, from 0.001% to 15%, from 0.025% to 10 from 0.05% to 10%, from 0.05% to 5%, or even from 0.1% to 5%, by weight of the total composition. A particular suitable vitamin $B_3$ compound is Niacinamide PC brand Niacinamide available from DSM.

Dermatologically Acceptable Carrier

The compositions herein may include a dermatologically acceptable carrier ("carrier") that provides a suitable matrix to store and deliver the actives (i.e., artichoke leaf extract and vitamin $B_3$ compound) and other optional ingredients. The phrase "dermatologically acceptable carrier", as used herein, means that the carrier is suitable for topical application to the keratinous tissue, has good aesthetic properties, is compatible with the actives in the composition, and will not cause any unreasonable safety or toxicity concerns. In one embodiment, the carrier is present at a level of from about 50% to about 99%, about 60% to about 98%, about 70% to about 98%, or, alternatively, from about 80% to about 95%, by weight of the composition.

The carrier can be in a wide variety of forms. Non-limiting examples include simple solutions (e.g., aqueous, organic solvent, or oil based), emulsions, and solid forms (e.g., gels, sticks, flowable solids, or amorphous materials). In certain embodiments, the dermatologically acceptable carrier is in the form of an emulsion. Emulsion may be generally classified as having a continuous aqueous phase (e.g., oil-in-water and water-in-oil-in-water) or a continuous oil phase (e.g., water-in-oil and oil-in-water-in-oil). The oil phase herein may comprise silicone oils, non-silicone oils such as hydrocarbon oils, esters, ethers, and the like, and mixtures thereof.

The aqueous phase typically comprises water. However, in other embodiments, the aqueous phase may comprise components other than water, including but not limited to water-soluble moisturizing agents, conditioning agents, antimicrobials, humectants and/or other water-soluble skin care actives. In one embodiment, the non-water component of the composition comprises a humectant such as glycerin and/or other polyols. However, it should be recognized that the composition may be substantially (i.e., less than 1% water) or fully anhydrous.

A suitable carrier is selected to yield a desired product form. Furthermore, the solubility or dispersibility of the components (e.g., extracts, sunscreen active, additional components) may dictate the form and character of the carrier. In one embodiment, an oil-in-water or water-in-oil emulsion is preferred.

Emulsions may further comprise an emulsifier. The composition may comprise any suitable percentage of emulsifier to sufficiently emulsify the carrier. Suitable weight ranges include from about 0.1% to about 10% or about 0.2% to about 5% of an emulsifier, based on the weight of the composition. Emulsifiers may be nonionic, anionic or cationic. Suitable emulsifiers are disclosed in, for example, U.S. Pat. Nos. 3,755,560, 4,421,769, and *McCutcheon's Detergents and Emulsifiers*, North American Edition, pages 317-324 (1986). Suitable emulsions may have a wide range of viscosities, depending on the desired product form.

The carrier may further comprise a thickening agent as are well known in the art to provide compositions having a suitable viscosity and rheological character.

Optional Components

In some embodiments, the inventive composition herein may include one or more optional components known for use in topical cosmetic compositions, provided the optional components do not unacceptably alter the desired benefits of the composition. The optional components, when present, may be included at an amount of about 50%, 40%, 30%, 20%, 10%, 5%, or 3%, by weight of the composition, for example, at least about 0.001%, 0.01%, 0.1%, 0.2%, 0.5%, or 1%, by weight of the composition. Suitable ranges include any combination of the lower and upper limits including suitable ranges from about 0.1% to about 50%; from about 0.2% to about 20%; or from about 1% to about 10%, by weight of the composition.

The optional components, when incorporated into the composition, should be suitable for use in contact with human skin tissue without undue toxicity, incompatibility, instability, allergic response, and the like. Nonlimiting examples of optional components include additional skin anti-aging agents, skin tone agents, anti-inflammatory agents, sunscreen actives, anti-acne actives, desquamation actives, anti-cellulite agents, chelating agents, flavonoids, tanning active, non-vitamin antioxidants and radical scavengers, hair growth regulators, anti-wrinkle actives, anti-atrophy actives, minerals, phytosterols and/or plant hormones, N-acyl amino acid compounds, antimicrobial or antifungal actives, and other useful skin care actives, which are described in further detail in U.S. Publication Nos. US2006/0275237A1 and US2004/0175347A1.

The Personal Care Product Council's *International Cosmetic Ingredient Dictionary and Handbook*, Thirteenth Edition, describes a wide variety of non-limiting cosmetic and pharmaceutical ingredients commonly used in the skin care industry, which are suitable optional components for use in the compositions of the present invention. Examples of these ingredient classes include: abrasives, absorbents, aesthetic components such as fragrances, pigments, colorings/colorants, essential oils, anti-caking agents, antifoaming agents, antimicrobials, binders, biological additives, buffering agents, bulking agents, chelating agents, chemical additives, colorants, cosmetic astringents, cosmetic biocides, denaturants, drug astringents, emollients, external analgesics, film formers or materials, opacifying agents, pH adjusters, preservatives, propellants, reducing agents, sequestrants, skin cooling agents, skin protectants, thickeners viscosity modifiers, vitamins, and combinations thereof.

Suitable skin tone agents include, but are not limited to, sugar amines, arbutin, deoxyarbutin, 1,3-dihydroxy-4-alkylbenzene such as hexylresorcinol, sucrose dilaurante, bakuchoil (4-[(1E, 3S)-3-ethenyl-3,7-dimethyl-1,6 octadienyl] phenol or monterpene phenol), pyrenoine (available from Biotech Marine, France), *Panicum miliaceum* seed extract, arlatone dioic acid, cinnamic acid, ferulic acid, achromaxyl, methyl nicotinamide, oil soluble licorice extract, folic acid, undecylenic acid (i.e., undecenoic acid), zinc undecylenate, thiamine (Vitamin B1) and its hydrochloride, L-tryptophan, *Helianthus annuus* (sunflower) and *Vitis vinifera* (grape) leaf extract, carnosine (i.e., dragosine), methyl gentisate, 1,2-hexandiol and 1,2-octandiol (i.e., combination sold as Symdiol 68 by Symrise AG, Germany), inositol, decylenoylphenylalanine (e.g., sold under the tradename Sepiwhite by Seppic, France), kojic acid, hexamidine compounds, salicylic acid, and retinoids including retinol and retinyl propionate.

One or more anti-inflammatory agents may be included in the present composition for improving the appearance of hyperpigmentation resulting from skin inflammation. Transient inflammatory events triggering hyperpigmentation and, more specifically, post-inflammatory hyperpigmentation include, but are not limited to, acne lesions, ingrown hairs, scratches, insect bites, surfactant damage, allergens, and short-term UV exposure. Inflammation induced hyperpigmentation including post-inflammatory hyperpigmentation may be managed by incorporating into the compositions herein an anti-inflammatory agent. When present, the compositions herein contain up to about 20%, 10%, 5%, 3%, or 1% by weight of the composition, of the anti-inflammatory agent. When present, the compositions herein contain at least about 0.001%, 0.01%, 0.1%, 0.2%, 0.3%, 0.5%, or 1%, by weight of the composition, of the anti-inflammatory agent. Suitable ranges include any combination of the lower and upper limits. Suitable anti-inflammatory agents include, but are not limited to nonsteroidal anti-inflammatory agents (NSAIDS including but not limited to ibuprofen, naproxen, flufenamic acid, etofenamate, aspirin, mefenamic acid, meclofenamic acid, piroxicam and felbinac), glycyrrhizic acid (also known as glycyrrhizin, glycyrrhixinic acid, and glycyrrhetinic acid glycoside) and salts such as dipotassium glycyrrhizate, glycyrrhetenic acid, licorice extracts, bisabolol (e.g., alpha bisabolol), manjistha (extracted from plants in the genus *Rubia*, particularly *Rubia cordifolia*), and guggal (extracted from plants in the genus *Commiphora*, particularly *Commiphora mukul*), *kola* extract, chamomile, red clover extract, and sea whip extract (extracts from plant in the order Gorgonacea), derivatives of any of the foregoing, and mixtures thereof.

The compositions herein may include one or more sunscreen actives (or sunscreen agents) and/or ultraviolet light absorbers. Herein, "sunscreen active" collectively includes sunscreen actives, sunscreen agents, and/or ultraviolet light absorbers. Sunscreen actives include both sunscreen agents and physical sunblocks. Sunscreen actives may be organic or inorganic. Examples of suitable sunscreen actives are disclosed in Personal Care Product Council's *International Cosmetic Ingredient Dictionary and Handbook*, Thirteenth Edition, as "sunscreen agents." Particularly suitable sunscreen actives are 2-ethylhexyl-p-methoxycinnamate (commercially available as PARSOL™ MCX), 4,4'-t-butyl methoxydibenzoyl-methane (commercially available as PARSOL™ 1789), 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl))aminobenzoate, 2-ethylhexyl-2-cyano-3,3-diphenylacrylate, 2-ethylhexyl-salicylate, glyceryl-p-aminobenzoate, 3,3,5-tri-methylcyclohexylsalicylate, menthyl anthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene, zinc oxide, benzylidene camphor and derivatives thereof, titanium dioxide, and mixtures thereof.

In one embodiment, the composition may comprise from about 1% to about 20%, and alternatively from about 2% to about 10% by weight of the composition, of the sunscreen active. Exact amounts will vary depending upon the chosen sunscreen active and the desired Sun Protection Factor (SPF), which is within the knowledge of one of skilled in the art.

II. Methods of Use

Various methods of treatment, application, regulation, or improvement may utilize the aforementioned compositions. Identification of a region of aging skin may occur on any skin surface of the body. Skin surfaces of the most concern tend to be those not typically covered by clothing such as facial skin surfaces, hand and arm skin surfaces, foot and leg skin surfaces, and neck and chest skin surfaces. In particular, identification of the region of aging skin may be on a facial skin surface including the forehead, perioral, chin, periorbital, nose, and/or cheek skin surfaces. The target skin surface may include any sign of skin aging known in the art (e.g., fine lines, deep lines, wrinkles, course texture, sagging, unfirm skin and lack of elasticity).

The method may include applying the composition to the previously identified area of aging skin, or an area where one seeks to prevent the appearance of aging skin. Many regimens exist for the application of the composition. The composition may be applied at least once a day, twice a day, or on a more frequent daily basis, during a treatment period. When applied twice daily, the first and second applications are separated by at least 1 to 12 hours. Typically, the composition may be applied in the morning and/or in the evening before bed.

The treatment period is ideally of sufficient time for the combination of vitamin $B_3$ compound and artichoke leaf extract to provide an improvement in the appearance of aging skin. The treatment period may be at least 1 week, and in some embodiments the treatment period may last about 4 weeks, 8 weeks, or 12 weeks. In certain embodiments, the treatment period will extend over multiple months (i.e., 3-12 months) or multiple years. In one embodiment the composition is applied at least once a day during a treatment period of at least 4 weeks, 8 weeks, or 12 weeks. In one embodiment the composition is applied twice a day during a treatment period of at least 4 weeks, 8 weeks, or 12 weeks.

The step of applying the composition may be accomplished by localized application. In reference to application of the composition, the terms "localized", "local", or "locally" mean that the composition is delivered to the targeted area (e.g., wrinkles around the eyes) while minimizing delivery to skin surface not requiring treatment. The composition may be applied and lightly massaged into area of aging skin. The form of the composition or the dermatologically acceptable carrier should be selected to facilitate localized application. While certain embodiments herein contemplate applying a composition locally to an area, it will be appreciated that compositions herein can be applied more generally or broadly to one or more skin surfaces.

In some embodiments, the composition may be delivered by a variety of applicators appropriate for localized and general application. Such applicators can include droppers, applicator wands, cotton swabs, or any other suitable device. Other suitable applicators include SH-0127 pen applicator available from Shya Hsin Plastic Works, Inc., Taiwan and either the Xpress Tip or liquid filled swab available from SwabPlus, Inc., China. The applicator may be configured to easily apply the composition to signs of aging, such as fine lines and wrinkles, and allowing for a dosed amount of the composition of between about 1 to about 50 uL/cm$^2$ or between about 1 to about 5 uL/cm$^2$. In another embodiment, the composition is applied to the one or more signs of aging and more generally to one or more facial skin surfaces contemporaneously (i.e., over a period of less than 30 minutes or, more typically, less than 5 minutes). It is to be appreciated that the compositions herein may also be applied directly by using one's finger or in other conventional manners.

In one embodiment, the method comprises the steps of applying a first composition comprising an effective amount of artichoke leaf extract and vitamin $B_3$ compound in combination to a skin surface and of applying a second composition to the skin surface, before or after the first composition. The first and second compositions may be any compositions described herein; however, the second composition may optionally comprise an effective amount of the artichoke leaf extract and vitamin $B_3$ compound blend present in the first composition. The second composition may comprise one or more anti-aging agents, tone agents, sunscreen actives, anti-inflammatory agents, or optional components. The first composition may be generally or locally applied, while the second composition may be generally or locally applied to the skin surface including the aging skin to which the first composition is applied. In certain embodiments, the skin surface is facial skin surface which include one or more of the forehead, perioral, chin, periorbital, nose, and cheek skin surfaces. In another embodiment, the first and second compositions are applied contemporaneously to at least the cheek, forehead, and chin/perioral skin surfaces. For general application to a skin surface and, particularly a facial skin surface, the dosed amount of the first or second composition may be between about 1 to about 50 uL/cm$^2$ per application (i.e., per single application to the skin surfaces).

In certain embodiments, the artichoke leaf extract and vitamin $B_3$ compound may be included in two separate compositions that are used as part of a daily skin care regimen.

Suitable methods may comprise any one or more of the abovementioned steps. All of the aforementioned steps are applicable to application, treatment, regulation, and/or improvement of aging skin appearance. One suitable method of improving the appearance of aging skin includes the step of topically applying a composition comprising an effective amount of artichoke leaf extract and vitamin $B_3$ compound blend to the aging skin surface, wherein the composition is applied for a period of time sufficient to improve the appearance of the aging skin.

III. Mechanisms of Action

With aging, the protective function of the skin's epidermal barrier may become impaired. For example, the aging epidermal barrier may suffer increased permeability to harmful stimuli (e.g., free radicals), a reduction in the amount of lipid in the intercellular matrix, and/or a decreased capacity to diffuse toxins from deeper layers, which can lead to harmful stimuli penetrating the stratum corneum more easily. As a result, the underlying dermal layers may suffer increased damage such as, for example, degradation of collagen and elastin, and thinning of the stratum corneum. Thus, the recovery capacity of the epidermal barrier is substantially reduced, and the effects of aging may become visibly evident by the appearance of, for example, fine lines, wrinkles, and/or other textural signs of skin aging.

Up-regulation of NF-κB is associated with inflammation, which leads to impaired epidermal barrier function and the resulting appearance of textural signs of skin aging. Conversely, inhibition of NF-κB corresponds to an improved dermal matrix function, leading to improved textural appearance of the aging skin.

EXAMPLES

Example 1—Exemplary Compositions

Table 1 sets forth non-limiting examples of compositions suitable for use herein. The examples are given solely for the purpose of illustration and are not to be construed as limitations herein, as many variations thereof are possible without departing from the spirit and scope of the invention, which would be recognized by one of ordinary skill in the art. In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minor materials will vary depending on the physical and chemical characteristics of the particular ingredients selected to make the present invention as described herein.

All examples may be used to treat or improve the appearance of one or more signs of aging. The method herein may further relate to a regimen involving the localized treatment for one or more aging signs by a first composition (e.g., Examples A or B) and a more broad or general facial skin treatment by a second composition (e.g., Examples C, D or E), which can be applied before or after the localized treatment to improve a particular sign of aging (e.g., across the entire face).

TABLE 1

Exemplary Compositions

| Component/% by wt. | Example A | Example B | Example C | Example D | Example E |
|---|---|---|---|---|---|
| Artichoke Leaf Extract (Bio-Benefity ™, available from Ichimaru Pharcos Corp.) | 1.00 | 3.50 | 3.00 | 3.5 | 3 |
| Niacinamide (CAS No. 98-92-0) | 5.00 | 5.00 | 5.00 | 5.00 | 5.00 |
| Olive Oil Extract (OLIVEM 460, available from B&T Company) | 0.00 | 0.00 | 0.03 | 0.1 | 0.25 |
| N-Acetylglucosamine | 0.00 | 0.00 | 2.00 | 0.00 | 0.00 |
| Hexamidine Diisethionate | 0.00 | 0.00 | 0.09 | 0.09 | 0.00 |
| Sepiwhite ™ (Undecylenoyl-phenylalanine, neutralized) (available from SEPPIC) | 0.00 | 0.00 | 0.50 | 0.50 | 0.00 |
| Sepigel 305 ™ (Polyacrylamide + C13-14 isoparaffin + laureth-7) (available from SEPPIC) | 0.00 | 0.00 | 2.00 | 2.00 | 2.00 |
| Dipotassium Glycyrrhizate | 0.00 | 0.10 | 0.10 | 0.30 | 0.00 |
| Homosalate | 0.00 | 0.00 | 0.00 | 9.00 | 0.00 |
| Avobenzone | 0.00 | 0.00 | 0.00 | 3.00 | 0.00 |
| Octocrylene | 0.00 | 0.00 | 0.00 | 2.60 | 0.00 |
| Oxybenzone | 0.00 | 0.00 | 0.00 | 1.00 | 0.00 |
| Octisalate | 0.00 | 0.00 | 0.00 | 4.50 | 0.00 |
| Butylene Glycol (CAS No. 107-88-0) | 5.50 | 5.50 | 5.50 | 5.50 | 5.50 |
| Glycerin (CAS No. 56-81-5) | 2.50 | 2.50 | 7.50 | 7.50 | 10.00 |
| DC 1503 Fluid ™ (available from DowCorning) | 2.50 | 2.50 | 2.50 | 2.50 | 2.50 |
| Lubrajel Oil ™ (available from Sederma) | 1.44 | 1.44 | 1.44 | 1.44 | 1.44 |
| Phenonip XB ™ (available from Clariant) | 1.25 | 1.25 | 1.25 | 1.25 | 1.25 |
| D-panthenol (CAS No. 81-13-0) | 1.00 | 1.00 | 1.00 | 1.00 | 1.00 |
| Tospearl 2000 ™ (Polymethylsils esquioxane) (CAS No. 68554-70-1) (available from GE Silicones/Momentive) | 1.00 | 1.00 | 1.00 | 1.00 | 1.00 |
| DL-Alpha Tocopheryl Acetate (CAS No. 7695-91-2) | 0.50 | 0.50 | 0.50 | 0.50 | 0.50 |
| Prodew 400 ™ (available from Ajinomoto) | 0.50 | 0.50 | 0.50 | 0.50 | 0.50 |
| Pemulen TR-2 ™ (Acrylates/C10-30 Alkyl Acrylate Crosspolymer) (available from Noveon) | 0.25 | 0.25 | 0.25 | 0.25 | 0.25 |
| Polysorbate 20 (CAS No. 9005-64-5) | 0.25 | 0.25 | 0.25 | 0.25 | 0.25 |
| Sodium Metabisulfite (CAS No. 7681-57-4) | 0.25 | 0.25 | 0.25 | 0.25 | 0.25 |
| Allantoin (CAS No. 97-59-6) | 0.20 | 0.20 | 0.20 | 0.20 | 0.20 |
| Sodium Hydroxide (CAS No. 1310-73-2) (50% solution by weight in water) | 0.17 | 0.17 | 0.17 | 0.17 | 0.17 |
| Disodium EDTA (CAS No. 139-33-3) | 0.10 | 0.10 | 0.10 | 0.10 | 0.10 |
| Xanthan Gum (CAS No. 11138-66-2) | 0.05 | 0.05 | 0.05 | 0.05 | 0.05 |
| Sodium Hyaluronate (CAS No. 9067-32-7) | 0.01 | 0.01 | 0.01 | 0.01 | 0.01 |
| Water (CAS No. 7732-18-5) | QS | QS | QS | QS | QS |
| TOTAL (% by weight of total composition) | 100.00 | 100.00 | 100.00 | 100.00 | 100.00 |

The compositions herein are generally prepared by conventional methods such as are known in the art of making topical compositions. Such methods typically involve mixing of the ingredients in one or more steps to a relatively uniform state, with or without heating, cooling, application of vacuum, and the like. Typically, emulsions are prepared by first mixing the aqueous phase materials separately from the fatty phase materials and then combining the two phases as appropriate to yield the desired continuous phase. The compositions may be prepared to optimize stability (physical stability, chemical stability, photostability) and/or delivery of the active materials. This optimization may include appropriate pH (e.g., less than 7), exclusion of materials that can complex with the active agent and thus negatively impact stability or delivery (e.g., exclusion of contaminating iron), use of approaches to prevent complex formation (e.g., appropriate dispersing agents or dual compartment packaging), use of appropriate photostability approaches (e.g., incorporation of sunscreen/sunblock, use of opaque packaging), etc.

Example 2—NF-κB Inhibition Analysis

In this Example, the effect of an artichoke-vitamin $B_3$ blend on NF-κB inhibition is evaluated. The vitamin $B_3$ compound used is niacinamide.

In Vitro Method.

CellSensor™ NF-κB-bla HEK 293T cells were pre-incubated for 1 hour with actives, stimulated with TNFα, and then incubated. After 5 hours plates were analyzed with the ToxBLAzer Dual Screenkit from Invitrogen.

TABLE 2

Effect of Artichoke Leaf Extract and Vitamin $B_3$ Compound on NF-κB inhibition

|  | Artichoke Leaf Extract 1.0% [A] | Niacinamide 0.0005% [B] | Combination of Artichoke Leaf Extract 1.0% + Niacinamide 0.0005% [C] | Expected Additive Effect of Combination [Sum of A + B] |
|---|---|---|---|---|
| % inhibition of NF-κB | 5% | 47% | 86%** | 52% |

**Statistically significant p = 0.0237

As illustrated in Table 2, the combination of artichoke extract and vitamin $B_3$ compound synergistically increased the inhibition of NF-κB, which is associated with reduced inflammation, a healthy epidermal barrier and healthy, younger looking skin.

Example 3—Method of Treatment

A test subject topically applies a composition comprising 3.5% artichoke leaf extract, 5.0% vitamin $B_3$ compound, and a dermatologically acceptable carrier to the entire face at least once per day for 12 weeks. The subject's facial skin is evaluated at baseline, week 4, week 8, and week 12 of treatment. With product use, the appearance of signs of facial skin aging such as fine lines and wrinkles are reduced, as assessed by digital imaging, expert grading and/or self assessment.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments herein have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of improving the appearance of aging skin comprising:
   a. identifying a target portion of skin that exhibits a sign of aging skin; and
   b. applying a composition comprising 0.05% to 5%, by weight, of an artichoke leaf extract and 0.0001% to 15%, by weight, of a vitamin $B_3$ compound in combination to the target portion of skin for a period of time sufficient for the combination of artichoke leaf extract and vitamin $B_3$ compound to synergistically increase the inhibition of NF-kB.

2. The method of claim 1, wherein the portion of skin surface is facial skin.

3. The method of claim 2, wherein the facial skin is selected from the group consisting of forehead, perioral, chin, periorbital, nose, and cheek skin surfaces.

4. The method of claim 1, wherein the composition is applied at least once a day for at least four weeks.

5. The method of claim 1, wherein the vitamin $B_3$ compound is niacinamide.

6. The method of claim 1, wherein the composition further comprises at least one additional skin active selected from the group consisting of sunscreen actives, anti-inflammatory agents and skin tone actives.

7. The method of claim 1, wherein the improvement to the appearance of aged skin is selected from the group consisting of improving the appearance of wrinkles and coarse deep wrinkles, fine lines, skin lines, crevices, bumps, unevenness, roughness, loss of skin elasticity, sagging, unfirm skin, keratoses; abnormal differentiation, hyperkeratinization; elastosis, and collagen breakdown.

8. The method of claim 1, wherein the composition has a pH of less than 7 and excludes materials that can complex with the vitamin B3 compound and the artichoke leaf extract.

* * * * *